United States Patent [19]

Knauf et al.

[11] 4,252,809
[45] Feb. 24, 1981

[54] SUBSTITUTED PTERIDINE COMPOUNDS AND PHARMACEUTICAL COMPOSITIONS CONTAINING THE SAME

[75] Inventors: Heinrich Knauf, Freiburg-Ebnet; Ernst Mutschler, Mainz-Hechtsheim; Karl-Dieter Voelger, Darmstadt, all of Fed. Rep. of Germany

[73] Assignee: Röhm Pharma GmbH, Darmstadt, Fed. Rep. of Germany

[21] Appl. No.: 923,628

[22] Filed: Jul. 11, 1978

Related U.S. Application Data

[63] Continuation-in-part of Ser. No. 860,824, Dec. 15, 1977, abandoned.

[30] Foreign Application Priority Data

Jan. 3, 1977 [DE] Fed. Rep. of Germany ....... 2700073
May 31, 1978 [IT] Italy ............................... 62249 A/78

[51] Int. Cl.³ ............................................. A61K 31/52
[52] U.S. Cl. .................................... 424/253; 544/260
[58] Field of Search ......................... 544/260; 424/253

[56] References Cited

U.S. PATENT DOCUMENTS

| | | | |
|---|---|---|---|
| 3,081,230 | 3/1963 | Weinstock et al. | 544/260 |
| 3,256,283 | 6/1966 | Osdene et al. | 544/260 |
| 4,077,957 | 3/1978 | Piper | 544/260 |
| 4,118,492 | 10/1978 | Voelger et al. | 424/251 |

OTHER PUBLICATIONS

Weinstock et al, J. Med. Chem. II, pp. 573–578, (1968).

*Primary Examiner*—Nicholas S. Rizzo
*Attorney, Agent, or Firm*—Curtis, Morris & Safford

[57] ABSTRACT

Pharmaceutical compositions having a diuretic effect and containing as the active ingredient a compound of the formula

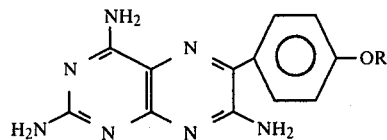

wherein R is hydrogen, a pharmaceutically acceptable cation, methyl, or a hydrophilic group R', are disclosed, as are novel compounds wherein R is R'.

12 Claims, No Drawings

SUBSTITUTED PTERIDINE COMPOUNDS AND PHARMACEUTICAL COMPOSITIONS CONTAINING THE SAME

This application is a continuation-in-part of application Ser. No. 860,824 filed Dec. 15, 1977, now abandoned.

The present invention relates to certain pharmaceutically-active substituted pteridine compounds, to pharmaceutical preparations containing these and related compounds, and to methods of treatment utilizing such compounds and compositions. More in particular, the substituted pteridine compounds of the invention have a diuretic and anti-hypertonic effect, and are also suitable for cardiac and coronary therapy.

The classic field of use for diuretically-active substances is in the treatment of edema. Relatively good therapeutic results have been achieved using, for example, saluretics (more precisely: materials which achieve a salt-separating effect directly by inhibition of sodium backresorption in the kidney tubules and which predominantly separate chloride ion as the anion).

With the discovery of the blood pressure lowering properties of saluretics, their field of use was considerably broadened. In particular, in the treatment of essential hypertonia, which is not susceptible to any causal treatment and accounts for about 80 percent of all hypertonia, saluretics have an established place. Important representatives of this group are the benzothiadiazine derivatives such as chlorothiazide and hydrochlorothiazide. Because of their influence on the electrolyte balance in patients, the use of benzothiazine derivatives is subject to severe restrictions. If liver or kidney disease is present, therapy with this class of active agents involves serious risk. In addition, dangerous disturbances of the electrolyte balance and liquid balance (hypochloremia, hypocalcemia, hypokalemia, and alkalosis) may develop on continued use. A loss of potassium ion is particularly undesirable during the monotherapeutic use of saluretics.

For this reason, the "potassium-sparing" diuretics were developed. One means of achieving this goal is in a competitive inhibition of the adrenocortical hormone aldosterone, which (and this is physiologically meaningful in normal metabolism) promotes the back-resorption of sodium and the secretion of potassium in the kidney tubules. This goal has been partly achieved by the use of the steroid derivative spironolactone. However, this therapy requires large doses (0.2–1 g per day). As further "potassium sparing" diuretics, which, however, are effective other than because of a competitive aldosterone inhibition, amiloride (N-amidino-3,5-diamino-6-chloropyrazine-carboxamide) and triamterene (2,4,7-triamino-6-phenylpteridine) have been found.

Triamterene has proved to be an extremely valuable active agent when used monotherapeutically as well as in combination, for example with saluretics, in the therapy of edema and high blood pressure. As a result, extensive investigations have been undertaken concerning the activity mechanism and metabolism of triamterene. Model tests on the main excretory duct of the salivary gland of rats (the epithelium of which functionally resembles that of the distal kidney tubule) have shown that triamterene completely blocks the back-resorption of sodium ion and reduces potassium ion secretion by one-half. The model test on the salivary gland excretory duct is in full agreement with findings in the kidney and can be viewed as an indicator of a "potassium sparing" diuretic effect of a type like that found in triamterene [cf. H. Knauf et al., Europ. J. Clin. Invest 6, 43 (1976)]. In addition, triamterene shows a cardio-protective effect. An anti-arrhythmic effect for triamterene can be demonstrated by electrophysiologic measurements on individual myocardial fibers of the isolated papillary muscle of guinea pigs [B. Luederitz et al., Verh. Dtsch. Ges. Kreislaufforschung 41, 305 (1975)].

Although triamterene fills quite well the therapeutic demands made on a diuretic, also from the point of view of its side effects, the search for still-better active materials continues. A disadvantage of triamterene which is not to be overlooked is, for example, a very small solubility in water which effectively makes parental application impossible. Thus, proceeding from the pteridine skeleton, investigations involving a systematic variation of substituents have been carried out on the connection between structure and (diuretic) effect [J. Weinstock et al., J. Med. Chem. 11, 573–579 (1968)].

In these investigations, 2,4,7-triamino-6-(p-hydroxyphenyl)-pteridine, one of the known metabolities of triamterene, has been involved. However, the findings missed observing the diuretic effects of this compound (Weinstock et al., loc. cit., 578 et seq.).

To the extent that the triamterene derivatives which were investigated showed a diuretic effect worth mentioning, such compounds as had non-polar substituents, for example, the p-toluyl-homolog of triamterene, were involved. Derivatives having polar groups, such as an amino group or a nitro group, in contrast are diuretically ineffective according to the finding of Weinstock (loc.cit., Table VIII).

It has now been found that, surprisingly, 2,4,7-triamino-6-(p-hydroxyphenyl)-pteridine exhibits an outstanding diuretic and potassium-retaining effect, even in small concentrations. The potassium-sparing effect is, in quantitative tests, more pronounced than that of triamterene. 2,4,7-triamino-6-(p-hydroxyphenyl)-pteridine also has an improved water solubility, particularly in the form of its physiologically acceptable salts, in comparison with the nonhydroxylated skeleton (triamterene).

Accordingly, one feature of the present invention concerns pharmaceutical preparations containing 2,4,7-triamino-6-(p-hydroxyphenyl)-pteridine, its known methyl ether, and/or physiologically-acceptable salts thereof as the active ingredient, i.e. compounds of the formula

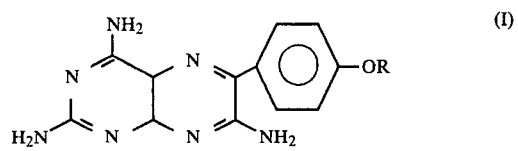

wherein R is hydrogen, methyl, or an anion.

Another feature of the invention concerns the discovery of compounds wherein group R is a hydrophilic group, R', other than —SO$_3$H or salts thereof, which compounds have pharmaceutically valuable properties like those of the known compounds discussed above. Those of the new compounds which have improved water solubility, not only in comparison with triamterene but also in comparison with the compounds of formula (I), are particularly preferred.

The compounds of formula (I) can be prepared by known processes. The preparation of novel compounds wherein R is R' can also proceed in known fashion, for example.

(a) by reaction of the 2,4,6-triamino-5-nitrosopyrimidine of the formula (II)

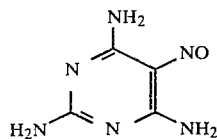

with a phenylacetonitrile compound of the formula

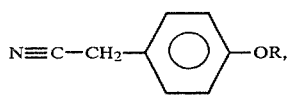

or, as a less generally-applicable method, (b) by the reaction, in the presence of an acid acceptor, of a compound of the formula

RX,     (IV)

wherein X is a group capable of entering into acylation and/or alkylation reactions, preferably chlorine or bromine, with a compound as in formula (I) wherein R is hydrogen or an alkali cation such as sodium or potassium. If group R' has a terminal carbonyl group, i.e. is of the structure

then X may also have the preferred structure

wherein R″ and R‴ are generally the same (i.e. R'X is an acid anhydride).

The hydrophilic group R' may be of the most varied structure, i.e. R' is:

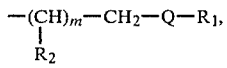     (a)

wherein
m is 0, 1, 2, or 3,
$R_1$ is hydrogen, methyl, or ethyl,
$R_2$ is hydrogen, —OH, or alkyl having 1 to 4 carbon atoms,
Q is oxygen, sulfur, or —$NR_3$, where $R_3$=$R_1$, or
Q together with $R_1$, forms an ammonium ion —$N(R_1)_3^+ Z^-$, where Z is a pharmaceutically acceptable anion, or
Q, together with $R_1$, is morpholinyl, pyrrolidinyl, piperidinyl, or piperazinyl; or

     (b)

wherein
n is 0, 1, 2, 3, or 4 and
Y is
—OH or a pharmaceutically acceptable salt thereof, or
—$NR_4R_5$, wherein $R_4$ and $R_5$ are the same or different and are hydrogen or straight-chain or branched alkyl having 1 to 4 carbon atoms, or
—(O)$_r$—$R_6$, wherein r is 0 or 1 and $R_6$ is alkyl having 1 to 6 carbon atoms, or
—($CH_2$)$_q$—$R_7$ wherein q is 0, 1, or 2 and $R_7$ is morpholinyl, pyrrolidinyl, piperidinyl, or piperazinyl bound by a carbon atom thereof or, when q is not 0, $R_7$ can also be —OH, or

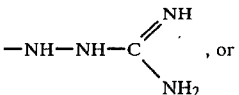

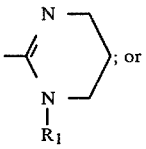

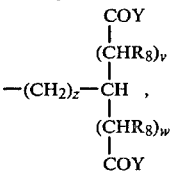     (c)

wherein
v, w, and z are the same or different and are 0, 1, or 2 and
$R_8$ is hydrogen or —OH; or

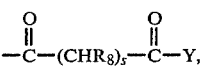     (d)

wherein s is 0, 1, 2 or 3; or

     (e)

wherein M is hydrogen, a pharmaceutically acceptable cation, chloro-substituted alkyl having 1 to 3 carbon atoms, or —$CH_2$—O—Ar, wherein Ar is phenyl or chloro-substituted phenyl.

The choice of the process to be employed for the manufacture of the hydrophilic compounds wherein R is R' and the reaction conditions depend, inter alia, on consideration of the relative accessibility of the respective starting products of the formulas (I), (II), (III), and (IV), as well as on the probability of the formation of by-products (e.g., by reaction of the amino function), and on the ease with which separation and purification can be carried out. For example, care should be taken that the substituents R are sufficiently stable under the conditions of the synthesis when using method variant (a).

The preparation of compounds wherein R=R' according to method (a) can be undertaken as follows: the compound of formula (II) is reacted at an elevated temperature, and optionally in suspension, with the compound of formula (III) in a suitable reaction medium which is inert under the reaction conditions, for example dimethylformamide or N,N-dimethyl-acetamide, preferably in the presence of an alkali metal hydroxide or alkali metal amide, or of an alkali metal alcoholate of a lower alcohol, for example, in an alkoxy-alkanol such as 2-ethoxyethanol, or in methanol.

The reaction time is as a rule kept as short as possible, for example when operating at reflux temperature. Working up can be accomplished according to the usual procedures.

Precautions can be taken against a decomposition to the educt and/or of the end product, for example by operating at the lower limit of the possible range of reaction temperatures, or by the use of alkali metal alcoholates which are little nucleophilic, such as potassium-tertbutoxide.

The preparation of compounds wherein R is R' according to method (b) can be undertaken as follows: A compound of formula (IV), optionally in a suitable solvent such as one of those mentioned below, and optionally with the addition of an acid acceptor such as a tertiary amine like triethylamine, N,N-diamethylaniline, or N-methylmorpholine, is added at a temperature between room temperature and 120° C., or at the boiling point of the solvent, preferably with stirring, to a compound of the formula (I), where R is hydrogen or an alkali metal cation, in a suitable inert solvent. Suitable solvents for the compound of formula (I) are, for example, a nitrile such as acetonitrile; an amide such as N,N-dimethylformamide or hexamethyl phosphoric acid triamide; an alcohol such as tert. butanol; or an amine such as pyridine or N,N-dimethylaniline. The compound may optionally be present in a mixture of such solvents, or also as a suspension.

For bringing the reaction to completion, the mixture is stirred for a certain period of time, for example, for from 2 to 24 hours, whereupon the batch can be worked up in the usual manner. When R in the compound of formula (I) is hydrogen, it can also be condensed with a carboxylic acid, i.e. a compound of the formula (IV) containing a —COOH group, using a condensing agent such as dicyclohexyl carbodiimide in a fashion known per se.

The starting compounds of formulas (I), (II), (III), and (IV) are known or can be prepared according to known methods, or they can be prepared by methods analogous to known methods.

The compounds of formula (I), including those where R50 R', are as a rule crystalline compounds of relatively high melting point (some with decomposition). They can, for example, be recrystallized from aqueous solution, optionally with the addition of formamide or acetonitrile, and optionally with the addition of acids such as formic, acetic, or phosphoric acid.

The compounds of formula (I) wherein R=H, i.e. 2,4,7-triamino-6-(p-hydroxyphenyl)-pteridine="p-hydroxytriamterene", and its physiologically acceptable salts, particularly the sodium, potassium, and lithium salts, as well as the salts with physiologically unobjectionable and pharmacologically similar amines and guanidines not having a contra-indicatory effect, for example N-alkylsubstituted ethanolamines and (basic) derivatives, as well as the propanol-2-amines and (basic) derivatives, are valuable pharmaceuticals, as are also the compounds of formula (I) wherein R is methyl or R'. They have an outstanding diuretic effect while at the same time being potassium-retentive, as well as having an extra-renal effect, particularly a cardio-protective effect. These effects cannot be viewed as being isolated from each other. Their fundamental mechanism is diuresis, with which an anti-hypertonic effect is coupled. The influence exercised on the general electrolyte balance of the patient can include an influence on the electrolyte balance of the myocardium, to which the cardio-protective effect can be attributed. The compounds thus show a complex of activities, among which the anti-hypertonic, and particularly the cardio-protective, can be more or less pronounced.

p-hydroxy-triamterene and its methyl ether are particularly preferred compounds. The compounds are superior to those known in the art, for example, triamterene, and thus constitute a genuine enrichment of the technology. For a direct comparison of the diuretic and potassium-retentive effect, investigations involving the epithelium of the main excretory duct of the glandula submaxillaris of rats according to Knauf (loc.cit.) will serve. The electrophysiological investigation of isolated heart structures of guinea pigs and dogs according to Luederitz (loc.cit.), for example, can be used as an indicator of the cardio-protective effect.

Superiority in comparison with triamterene arises from the better water solubility of the compounds of formula (I). Sharply improved water solubility is generally to be expected in those compounds of formula (I) which have groups with pronounced salt-forming properties (i.e. groups which are strongly basic or acidic).

From this viewpoint should particularly be mentioned those compounds of formula (I) in which R=R' and in which an amino group or an ammonium group stands in a position beta to phenolic oxygen. Those compounds wherein R' is —$(CH_2)_q$—$R_7$, wherein q is such that a nitrogen atom is found in the betaposition to phenoxy oxygen, are particularly mentioned.

The compounds of formula (I) are adaptable to use in therapeutic preparations suitable not only for oral, but also for parenteral, administration, particularly if they are in salt form.

The compounds of formula (I) can be administered in a total daily dosage of from 50 mg to 200 mg depending on the nature of the diagnosis and on individual requirements, taking into consideration the nature and severity of the disease and the age and disposition of the patent. These small amounts of active agents can be administered parenterally by infusion, for example.

As a result of the improved diuretic effect, in comparison with triamterene, the dose used in practice is as a rule lower than for triamterene; the normal dosages of triamterene can, thus, be viewed as the upper limits of the dosage region for the active agents of formula (I).

The new pharmaceutical preparations can be prepared in the usual ways and can contain the usual carriers and auxiliary agents. Solid compositions suitable for oral administration represent one embodiment of the invention, such as tablets, capsules, dragees, etc. For oral administration, the composition can contain pharmaceutically indifferent solids as carrier materials, for example, mannite, lactose, organic or inorganic calcium salts, etc. Polyvinyl pyrrolidone, gelatine, or cellulose derivatives are suitable, among others, as binders. As further additives, tablet cracking agents such as starch or alginic acid, lubricants such as stearic acid or its salts, and inorganic flow agents such as talc or colloidal silicic acid can be employed, as well as agents correcting the taste, and the like.

The active ingredient can be mixed with the auxiliaries in the usual manner and granulated when wet or dry. According to the kind of the additives which are employed, a powder which can be directly formed into tablets can also be obtained by a simple mixing. The granulate or powder can be filled directly into capsules or pressed into tablet cores in the usual manner.

For parenteral administration, the therapeutic agents can also be prepared and administered in the conventional manner.

A better understanding of the present invention and of its many advantages will be had by referring to the following examples, given by way of illustration:

EXAMPLE 1

Preparation of 2,4,7-triamino-6-(p-acetoxyphenyl)-pteridine 410 mg of metallic sodium are dissolved with stirring in 100 ml of 2-ethoxy-ethanol. 1100 mg of 2,4,6-triaminonitroso-pyrimidine and 1140 mg of p-acetoxybenzyl-cyanide are added with stirring one after the other and the mixture is heated to the boiling point with stirring. The color of the mixture changes from violet to brown. After two hours' boiling under reflux, heating is discontinued and the reaction mixture is left to cool. Subsequently, 70 to 80 percent of the 2-ethoxy-ethanol are drawn off using the vacuum from a water aspirator and the residue is combined with 500 ml of water. After extraction four times with ether, the extract is adjusted to pH 5 with 2 N hydrochloric acid. The precipitate is filtered off, washed with a little ice-cold acetone and recrystallized from 10 percent acetic acid. Further purification can follow using a silica gel column. The compound mentioned in the title is obtained, which compound decomposes (with charring) at 319°–321° C.

The reaction can advantageously also be carried out using an alkali alcoholate in methanol.

EXAMPLE 2

Preparation of 2,4,7-triamino-6-(p-methoxyphenyl)-pteridine 1.85 g of sodium (0.08 mol) were dissolved with stirring in 480 ml of ethylene glycol monoethyl ether (Baker, Analyzed Reagent, used without drying) present in a one-liter 3-necked flask. The solution was heated and then combined, one after the other, with 12 g of 2,4,6-triamino-5-nitrosopyrimidine (0.078 mol) and 11.85 ml (12.8 g) of p-methoxybenzylcyanide (0.087 mol). After about 15 minutes, the initially red-violet reaction mixture turned brown. After about 25 minutes, the mixture began to reflux and a brown crystalline precipitate formed. The batch was refluxed for another two hours. After cooling to room temperature, the precipitate was filtered off on a G 4 frit, washed with 220 ml of water, 100 ml of acetone, and 100 ml of ether, filtered to dryness and dried in vacuum over $P_4O_{10}$ until constant weight was reached.

Yield: 18.21 g (82.4 percent of theory).

Thin-layer chromatograph (butanone:acetone:water, 60:6:10): uniform.

Elemental analysis $C_{13}H_{13}N_7O$ (molecular weight = 283.30).

|       | C    | H   | N    |
|-------|------|-----|------|
| calc. | 55.1 | 4.6 | 34.6 |
| found | 55.3 | 5.5 | 34.9 |

EXAMPLE 3

Preparation of 2,4,7-triamino-6-(p-2-hydroxyethoxyphenyl)-pteridine 460 mg of metallic sodium are dissolved with stirring in 150 ml of 2-ethoxy-ethanol. 3.1 g (0.02 mol) of triaminonitroso-pyrimidine and 3.5 g (0.02 mol) of p-(2-hydroxyethoxy)phenyl-acetonitrile are added one after the other with stirring and the mixture is heated with stirring in a water bath at 60° C. The color of the mixture changes from violet to bright brown. After stirring for 14 hours, the reaction is over. The mixture is left to cool. Unreacted 2,4,6-triamino-nitrosopyrimidine is filtered off and the clear solution is concentrated to dryness. The precipitate is taken up in hot acetone and the crude product is precipitated by admixture with petroleum ether. Purification follows first by recrystallization from butanol and then by separation on a silica gel-dry column (silica gel 60 Merck). The compound mentioned in the title is obtained as yellow-brown crystals.

Melting point = 300°–302° C. (decomposition).

RF-value = 0.55, uniform in chloroform/methanol (70:30) on silica gel-thin layer plates.

$C_{14}H_{15}N_7O_2$ (molecular weight = 313.3).

EXAMPLE 4

Preparation of 2,4,7-triamino-6-(p-2,3-dihydroxypropoxyphenyl)-pteridine

The compound mentioned above can be prepared in a fashion analogous to the compound of Example 3.

Melting point = 278° C. (decomposition).

RF-value = 0.50, uniform in chloroform/methanol (70:30) on silica gel-thin layer plates.

$C_{15}H_{17}N_7O_3$ (molecular weight = 341.3).

EXAMPLE 5

Preparation of 2,4,7-triamino-6-(p-succinoylphenyl)-pteridine 0.63 g (0.0055 mol) of succinic acid, 1.35 g (0.005 mol) of p-hydroxytriamterene, and 1.12 g (0.05 mol) of dicyclohexylcarbodiimide are added to dry acetone and heated at the boiling point for 14 days with exclusion of water. The reaction is interrupted and the solvent removed. The precipitate so formed is washed several times with ether. The remaining precipitate is taken up in the least possible amount of DMF (5–10 ml) and diluted with a four-fold volume of acetone. The solution is introduced into a Sephadex-LH 20 column (product of the Pharmacia Company) suspended in acetone. On elution, the final product appears after a forefraction. It is recovered by concentration of the acetone solution.

Rf-value = 0.30 in chloroform/methanol (70:30) on silica gel-thin layer plates.

EXAMPLE 6

Preparation of
2,4,7-triamino-6-(p-adipinoylphenyl)-pteridine

The compound mentioned in the title can be prepared in a fashion analogous to the compound of Example 5.

Rf-value=0.31 in chloroform/methanol (70:30) on silica gel-thin layer plates.

The reagents of formula (III) can be prepared according to the following Examples, for instance:

EXAMPLE 7

Preparation p-(2-hydroxyethoxy)-phenylacetonitrile 5 g of p-hydroxyphenylacetonitrile are dissolved in 250 ml of methyl ethyl ketone. 7 g of 2-bromethanol and 23 g of potassium carbonate are added thereto. The mixture is heated for 48 hours under reflux with stirring. After the reaction is concluded, the potassium carbonate and potassium bromide which has formed are filtered off. The precipitate is washed with acetone and the acetone washing liquid is combined with the reaction mixture.

The clear solution is reduced in volume to about 10–15 ml. It is then taken up in ether and shaken with 0.01 N sodium hydroxide. The ether phase is dried over sodium carbonate and the ether is then distilled off. The compound of the title is obtained as a yellowish oil.

Rf-value=0.70 in acetone/carbon tetrachloride (1:1) on silica gel-thin layer plates.

EXAMPLE 8

Preparation of
p-(2,3-dihydroxypropoxy)-phenylacetonitrile p-(2,3-dihydroxypropoxy)-phenyl acetonitrile can also be prepared in the same way as p-(2-hydroxyethoxy)-phenylacetonitrile, in which case the extraction is with water instead of with sodium hydroxide. The product is found in the aqueous phase and, upon concentration thereof, precipitates as a colorless crystalline precipitate.

Rf-value=0.60 in acetone/carbon tetrachloride (1:1) on silica gel-thin layer plates.

The following examples serve to illustrate the preparation of therapeutic agents according to the invention.

EXAMPLE 9

Preparation of tablets resistant to stomach juice

For the preparation of the tablet cores, the following composition can be used:

15 mg of 2,4,7-triamino-6-(p-acetoxyphenyl)-pteridine as the active agent
10 mg of magnesium stearate
11 mg of talc
8 mg of "Aerosil"
95 mg of lactose granulate
55 mg of lactose (fine crystalline)
25 mg of cornstarch
80 mg of cellulose granulate.

The components are mixed in an intensive mixer (Loedige) and pressed to form tablets weighing 300 mg. Tablets are obtained which have a resistance to breaking of 6.5–8.5 (determined on an ERWEKA breaking-resistance tester. Decomposition in water at 37° C.=2.5 minutes).

For preparation of a coating resistant to stomach juices, a lacquer suspension is applied to the tablet cores.

Namely, a lacquer suspension containing the following components is applied to 4 kg of the cores prewarmed to 40° C.:

100 g of a polyacrylic resin dispersion containing 30 percent of solids
300 g of a pigment suspension containing 120 g of solids and
600 g of water.

The polyacrylic resin contains a copolymer of ethyl acrylate and methacrylic acid (1:1).

The pigment suspension has the following composition:

50 g of talc
63 g of titanium dioxide
42 g of coloring lacquer
90 g of polyethylene wax 600°, 33 percent in water
30 g of emulsifier ("Tween 80"), 33 percent in water
200 g of "Tylose C 30", 3 percent in water*
15 g of cellulose, fine crystalline
183 g of lactose
1 g of anti-foaming emulsion
326 g of water.

*a commercially-available cellulose ether.

After a spray time of about 40 minutes, tablets having a resistance to stomach juice of more than three hours are obtained.

Tablets can be prepared in the same way from compositions containing as the active ingredient 2,4,7-triamino-pteridine substituted in the 6-position with either p-hydroxyphenyl, p-methoxyphenyl, p-2-hydroxyethoxyphenyl, p-2,3-dihydroxypropoxyphenyl, p-succinoylphenyl, or p-adipinoylphenyl, for example.

EXAMPLE 10

Preparation of a pharmaceutical composition suitable for parenteral administration A pharmaceutical composition suitable for parenteral, particularly intravenous, administration can be prepared as follows:

10 ml of a 10 percent aqueous solution of dimethylaminoethanol are added to 25 mg of 2,4,7-triamino-6-(p-hydroxyphenyl)-pteridine. The active agent goes into solution in whole or in part. The mixture is then diluted to 100 ml with physiological salt solution. A clear, yellowish solution of pH 10.9 is obtained.

Other compounds, such as those mentioned above in Example 9, having different substituents in the 6-position can be formulated into a parenterally-administrable composition in a similar fashion.

EXAMPLE 11

Preparation of
2,4,7-Triamino-6-[4-($\beta$-dimethylamino-ethoxy)phenyl]-pteridine 0.03 mol of metallic sodium is dissolved with stirring in 150 ml of 2-ethoxyethanol. 3.1 g (0.013 mol) of 4-($\beta$-dimethylamino-ethoxy)-phenyl acetonitrile in the form of the hydrochloride are added with stirring followed by 1.45 g (0.01 mol) of 2,4,6-triamino-5-nitroso-pyrimidine. After stirring for 48 hours at 60°–65° C. excluding access of moisture, the mixture is centrifuged when still hot. Petroleum ether is added to the solution obtained until it becomes cloudy. The solution is kept refrigerated to complete precipitation. The precipitate is filtered off. It can be recrystallized from n-butanol.

The compound mentioned in the title is obtained in form of yellow crystals which melt at 278°–281° C. (decomp.)

Thin layer chromatography in methanol/chloroform/concentrated aqueous ammonia (4:4:1 v/v) on silica gel-thin layer plates: $R_f$-value=0.47.

EXAMPLE 12

Preparation of 2,4,7-Triamino-6-[4-(β-N-piperidinyl-ethoxy)-phenyl]-pteridine

The title compound can be produced in a fashion analogous to that described in Example 7 using p-(β-N-piperidinylethoxy)-phenyl-acetonitrile. Thin layer chromatography in the same solvent as in Example 11:$R_f$-value=0.64.

EXAMPLE 13

Preparation of phenylacetonitriles of formula III

The preparation of these compounds is illustrated with reference to the preparation of basic compounds such as p-(β-amino-ethoxy)-phenylacetonitrile.

0.05 mol of β-chloroethylamine, preferably in salt form such as the hydrochloride, and 0.1 mol of dry potassium carbonate are added to 0.04 mol of p-hydroxyphenylacetonitrile in 200 ml of dry acetone. The mixture is stirred at 40°–45° C. for 24 hours and for another two hours at about the boiling temperature. The acetone is evaporated off. The residue is dissolved in 100 ml of water and concentrated hydrochloric acid is added until a pH of 1–2 is reached. The solution is extracted with three 100 ml portions of ether. The ether extract contains unreacted phenol, which may be recycled.

About 8N aqueous potassium hydroxide solution is added to the extracted aqueous solution until a pH of about 12 is reached.

The solution is again extracted with one portion of ether. The ether extract is dried with sodium carbonate. The salt of the basic nitrile is precipitated by passing dry hydrogen chloride into the solution.

The crystalline substances may be recrystallized, e.g. from ethanol/ethyl acetate.

In this way the following compounds of formula III have been obtained:
p-(β-dimethylamino-ethoxy)-phenylacetonitrile and its hydrochloride
p-(β-N-piperidinyl-ethoxy)-phenylacetonitrile and its hydrochloride.

EXAMPLE 14

Preparation of 2,4,7-triamino-6-(p-pivaloylphenyl)-pteridinetrifluoroacetate

A solution of hydroxytriamterene (0.016 m) in trifluoroacetic acid was acrylated with trimethylacetyl chloride (0.02 m) at ambient temperature for 60 hours. After removal of solvent and washing with acetonitrile, a 50 percent yield of solid melting at 281°–4° C. was obtained. The compound may be freed from trifluoroacetic acid in manner known per se.

EXAMPLE 15

Preparation of 2,4,7-triamino-6-(p-propoxycarbonyloxyphenyl)pteridine

Hydroxytriamterene (0.0186 m) was dissolved in hot dimethylformamide and treated with triethylamine (0.0376 m) at 35° C., propyl chloroformate (0.0376 m) at 10° C. and then stirred at ambient temperature for 3 days to give a 71 percent yield of material melting at 302°–8° C. after washing with water.

What is claimed is:

1. A parenterally administrable pharmaceutical composition for inducing diuresis, said composition comprising a pharmaceutically acceptable carrier for parenteral administration and a diuretically-effective amount of a compound of the formula

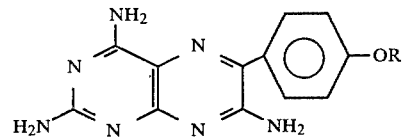

wherein R is hydrogen or a pharmaceutically acceptable cation.

2. A composition as in claim 1 wherein said compound is 2,4,7-triamino-6-(p-hydroxyphenyl)-pteridine.

3. The method of inducing diuresis in a patient which comprises parenterally administering to said patient a diuretically-effective amount of a compound of the formula

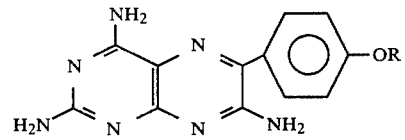

wherein R is hydrogen, or a pharmaceutically acceptable cation.

4. A compound of the formula

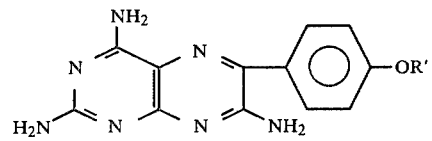

wherein
R' is

wherein
m is 0, 1, 2, or 3,
$R_1$ is hydrogen, methyl, or ethyl,
$R_2$ is hydrogen, —OH, or alkyl having 1 to 4 carbon atoms,
Q is oxygen, sulfur, or —$NR_3$, where $R_3$=$R_1$, or
Q together with $R_1$, forms an ammonium ion —$N(R_1)_3^+Z^-$, where Z is a pharmaceutically acceptable anion, or Q, together with $R_1$, is morpholinyl, pyrrolidinyl, piperidinyl, or piperazinyl; or

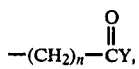 (b)

wherein n is 0, 1, 2, 3, or 4 and

Y is
—OH or a pharmaceutically acceptable salt thereof, or
—$NR_4R_5$, wherein $R_4$ and $R_5$ are the same or different and are hydrogen or straight-chain or branched alkyl having 1 to 4 carbon atoms, or
—$(O)_r$—$R_6$, wherein r is 0 or 1 and $R_6$ is alkyl having 1 to 6 carbon atoms, or
—$(CH_2)_q$—$R_7$ wherein q is 0, 1, or 2 and $R_7$ is morpholinyl, pyrrolidinyl, piperidinyl, or piperazinyl bound by a carbon atom thereof or, when q is not 0, $R_7$ can also be —OH, or

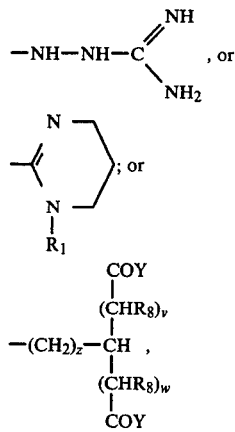 (c)

wherein v, w, and z are the same or different and are 0, 1, or 2 and $R_8$ is hydrogen or —OH; or

 (d)

wherein s is 0, 1, 2 or 3; or

 (e)

wherein

M is hydrogen, a pharmaceutically acceptable cation, chloro-substituted alkyl having 1 to 3 carbon atoms, or —$CH_2$—O—Ar, wherein Ar is phenyl or chloro-substituted phenyl.

5. A compound as in claim 4 which is 2,4,7-triamino-6-(p-acetoxyphenyl)-pteridine.

6. A compound as in claim 4 which is 2,4,7-triamino-6-(p-succinoylphenyl)-pteridine.

7. A compound as in claim 4 which is 2,4,7-triamino-6-(adipinoylphenyl)-pteridine.

8. A compound as in claim 4 which is 2,4,7-triamino-6-(p-2-hydroxyethoxyphenyl)-pteridine.

9. A compound as in claim 4 which is 2,4,7-triamino-6-(p-2,3-dihydroxypropoxy-phenyl)-pteridine.

10. A pharmaceutical composition comprising a pharmaceutically acceptable carrier and a therapeutically-effective amount of a compound as in claim 4.

11. A composition as in claim 10 wherein said compound is 2,4,7-triamino-6-(p-acetoxyphenyl)-pteridine.

12. The method of inducing diuresis in a patient which comprises orally or parenterally administering to said patient a diuretically-effective amount of a compound as in claim 4.

* * * * *